(12) United States Patent
Gleason

(10) Patent No.: US 12,409,048 B2
(45) Date of Patent: Sep. 9, 2025

(54) KNIT SPINAL IMPLANT RETENTION AND RELEASE SYSTEM AND METHOD

(71) Applicant: Spineology Inc., St. Paul, MN (US)

(72) Inventor: Joseph E. Gleason, Eagan, MN (US)

(73) Assignee: Spineology Inc., St. Paul, MN (US)

( * ) Notice: Subject to any disclaimer, the term of this patent is extended or adjusted under 35 U.S.C. 154(b) by 159 days.

(21) Appl. No.: 17/680,277

(22) Filed: Feb. 24, 2022

(65) Prior Publication Data
US 2022/0265438 A1 Aug. 25, 2022

Related U.S. Application Data

(60) Provisional application No. 63/153,166, filed on Feb. 24, 2021.

(51) Int. Cl.
*A61F 2/44* (2006.01)
*A61F 2/46* (2006.01)

(52) U.S. Cl.
CPC .......... *A61F 2/4455* (2013.01); *A61F 2/4611* (2013.01); *A61F 2002/4495* (2013.01); *A61F 2002/4629* (2013.01)

(58) Field of Classification Search
CPC ............ A61F 2/4611; A61F 2002/4627; A61F 2002/4628; A61F 2/4455; A61F 2002/4495; A61F 2002/4629
See application file for complete search history.

(56) References Cited

U.S. PATENT DOCUMENTS

| | | | | |
|---|---|---|---|---|
| 8,328,851 B2* | 12/2012 | Curran | ................. | A61F 2/4425 606/279 |
| 10,821,002 B1* | 11/2020 | Hibri | ...................... | A61F 2/441 |
| 2006/0206207 A1* | 9/2006 | Dryer | ..................... | A61F 2/446 606/104 |
| 2006/0293750 A1* | 12/2006 | Sherman | .................. | A61F 2/44 623/17.12 |
| 2010/0256766 A1* | 10/2010 | Hibri | .................... | A61F 2/4611 623/17.16 |
| 2013/0204370 A1* | 8/2013 | Danacioglu | ............ | A61F 2/447 623/17.16 |

* cited by examiner

Primary Examiner — Brian A Dukert
(74) Attorney, Agent, or Firm — Getz Balich LLC

(57) ABSTRACT

An implant retention system for a knit surgical implant can include an elongated hollow mesh tip, including a flanged section at a distal end thereof and an internal threaded section proximal to the flanged section, and an elongated hollow lock tube, including a non-threaded section at a distal end thereof and an external threaded section proximal to the non-threaded section. The mesh tip can be threaded over the lock tube to define a crimp section between the flanged section and the non-threaded section that engages a portion of the knit surgical implant to retain the knit surgical implant in engagement with the lock tube.

20 Claims, 4 Drawing Sheets

KNIT SPINAL IMPLANT RETENTION AND RELEASE SYSTEM AND METHOD

PRIORITY

This application claims the benefit of U.S. Provisional Application Ser. No. 63/153,166, filed on Feb. 24, 2021, which is hereby incorporated herein by reference in its entirety.

FIELD

The present invention generally relates to surgical instruments. More particularly, the present invention relates to instruments and methods for retaining a knit implant during a spinal surgical procedure.

BACKGROUND

Knit implants, such as disclosed in U.S. Pat. No. 5,549,679, are used in surgical procedures, such as spinal fusions. The knit implants are usually filled in situ with fill material or a variety of materials. The force required to fill and/or inflate the knit implant can make it difficult to retain the knit implant with respect to the filling instrument. Accordingly, there is a continuing need to enhance the retention of the knit implant during a filling procedure.

SUMMARY

Disclosed herein are devices, systems, instruments and methods of knit implant retention whereby the knit implant is entrapped between an inner tube (lock tube) and outer tube (mesh tip) tube via crimping the outer tube onto the knit implant after placement over the inserted inner tube.

The implant is released from the inner Lock Tube such that it is pulled back and out of the crimp zone of the mesh tip via an expanding inner tube grabbing instrument (lock tube puller). The lock tube puller utilizes frictional force between the device and the inner wall to bond the two together for withdrawal.

A male/female screw interface can be provided to accomplish the withdrawal of the inner lock tube out of the crimp zone, thereby simplifying the method and number of steps required to withdraw the Lock Tube.

An implant retention system for a knit surgical implant can include an elongated hollow mesh tip, including a flanged section at a distal end thereof and an internal threaded section proximal to the flanged section, and an elongated hollow lock tube, including a non-threaded section at a distal end thereof and an external threaded section proximal to the non-threaded section. The mesh tip can be threaded over the lock tube to define a crimp section between the flanged section and the non-threaded section that engages a portion of the knit surgical implant to retain the knit surgical implant in engagement with the lock tube.

The hollow mesh tip can include an external rib disposed adjacent to the proximal end thereof. A positioning retention tube can include a slot at a distal end thereof that is sized and shaped to mate with the proximal end of the hollow mesh tip.

The lock tube can include a slot defined in a proximal end thereof. A screw driver can include a male projection sized and shaped to engage the slot of the lock tube.

The knit surgical implant can be crimped between the flanged section of the mesh tip and the non-threaded section of the lock tube.

A spinal implant kit can be provided that includes a spinal fusion implant, the mesh tip instrument and the lock tube instrument. The kit can also include the screw driver instrument and/or the positioning retention tube. The spinal fusion implant can be a knit implant or other type of implant or a variety of different implants.

A method of operating spinal surgical instruments can include threading an elongated hollow mesh tip component over an elongated hollow lock tube component to locate a portion of a flexible spinal implant between a distal flanged section of the mesh tip and a distal non-threaded section of the lock tube, and crimping the flanged section towards the distal non-threaded section to secure the flexible spinal implant relative to the lock tube.

The method can also include engaging a screw driver with a proximal end of the lock tube and rotating the screw driver to unthread the lock tube from the mesh tip until the flexible spinal implant is no longer secured relative to the lock tube.

The method can also include engaging a positioning retention tube with a proximal end of the mesh tip to extend or project the lock tube into a disc space in a patient.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
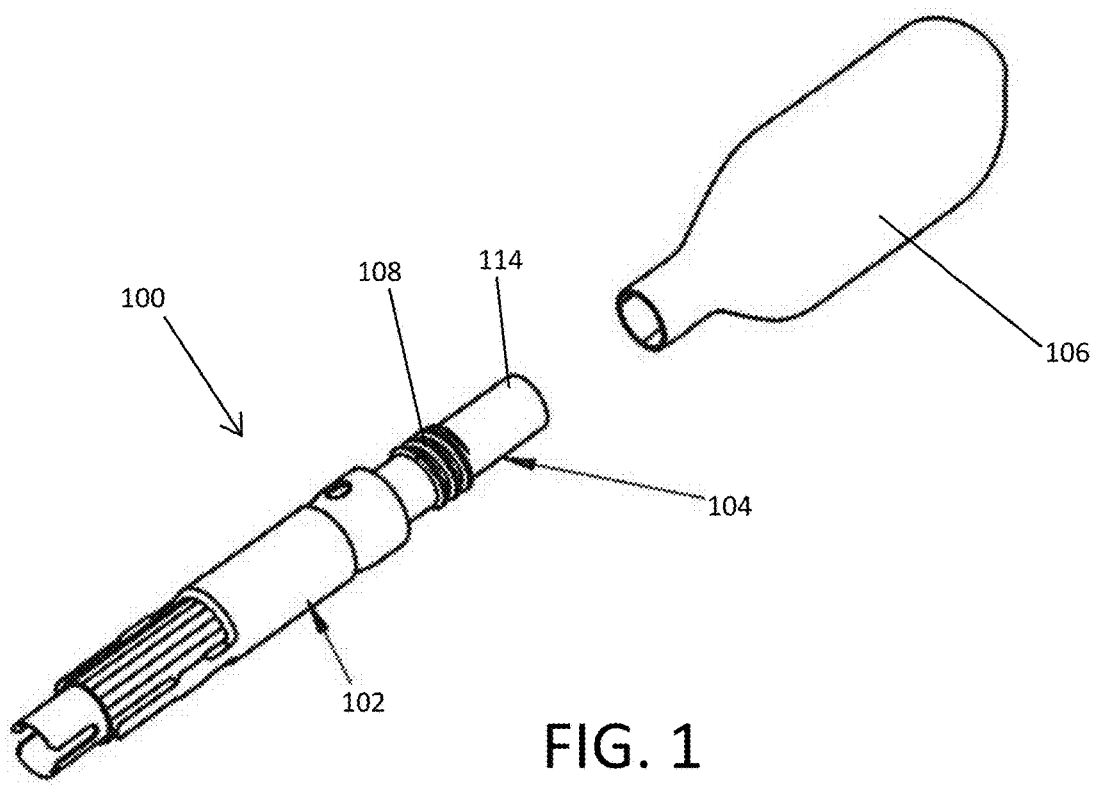
FIG. 1 is a perspective view of an implant retention system in accordance with embodiments of the present invention.
Figure 2:
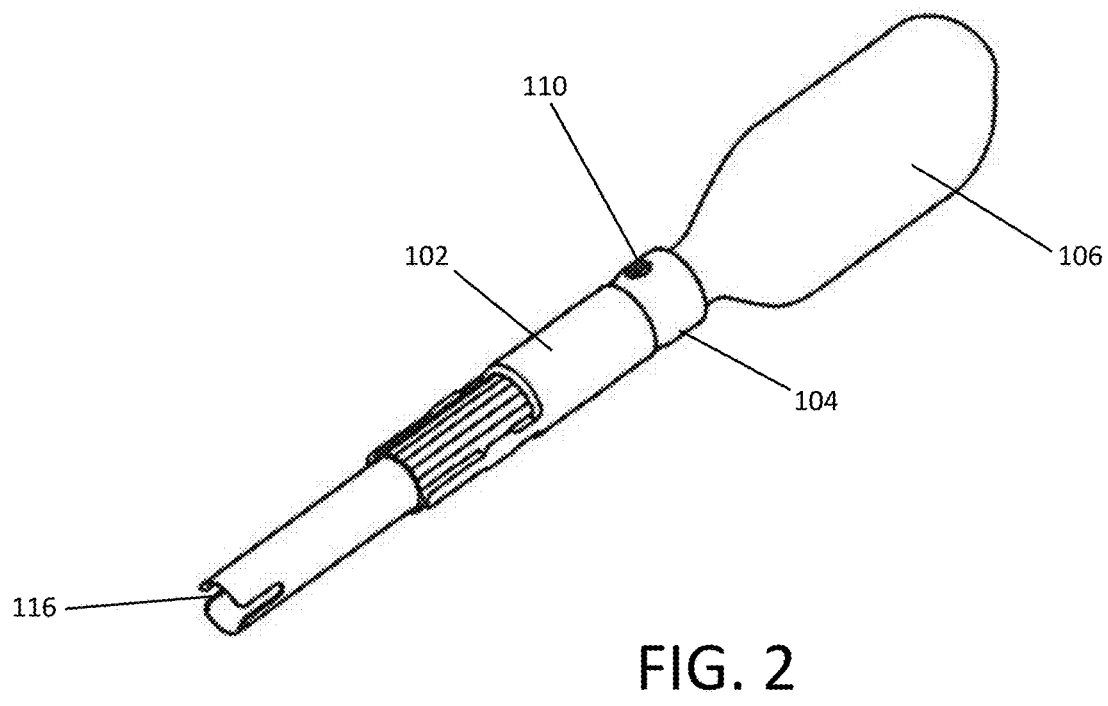
FIG. 2 is a perspective view of an implant retention system showing the implant attached thereto in accordance with embodiments of the present invention.
Figure 3:
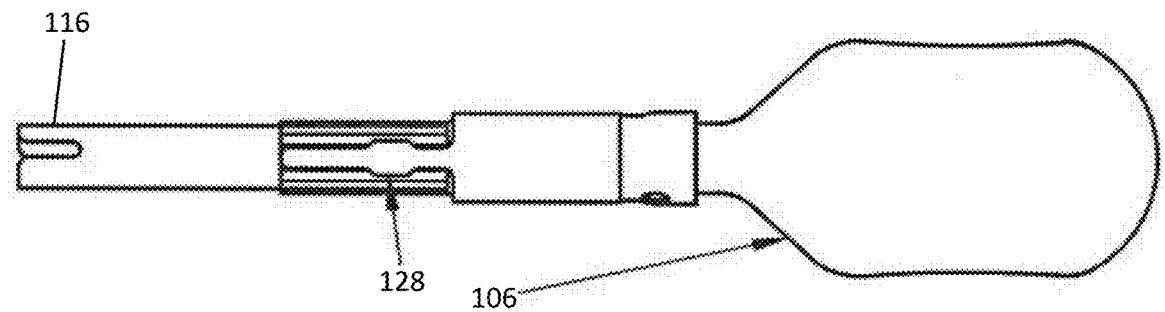
FIG. 3 is a top view of an implant retention system showing the implant attached thereto in accordance with embodiments of the present invention.
Figure 4:
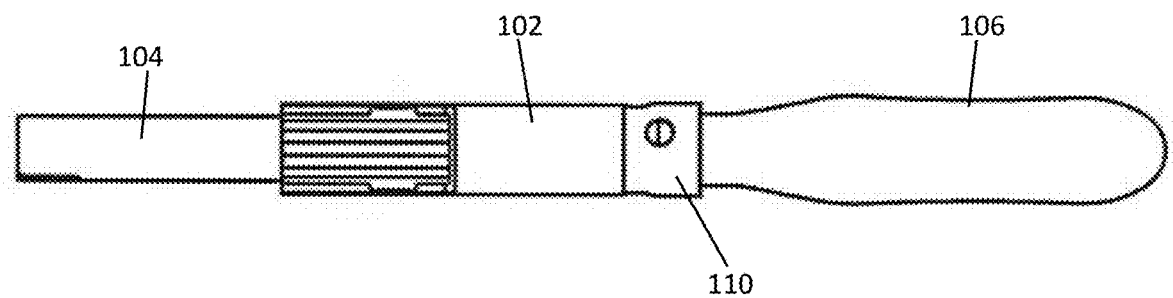
FIG. 4 is a side view of an implant retention system showing the implant attached thereto in accordance with embodiments of the present invention.
Figure 5:
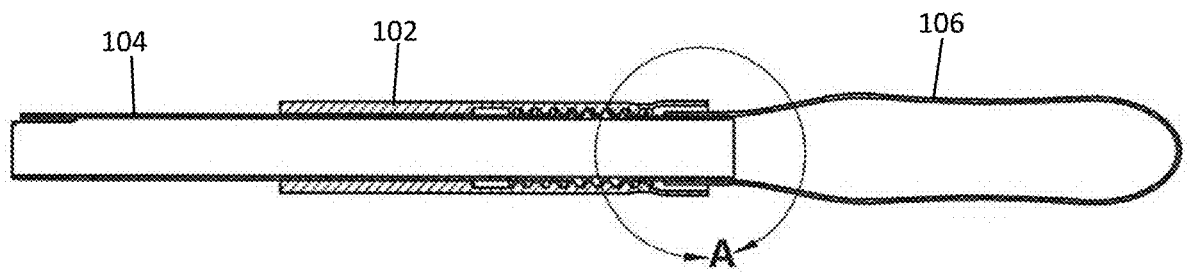
FIG. 5 is a side cross-sectional view of an implant retention system showing the implant attached thereto in accordance with embodiments of the present invention.
Figure 6:
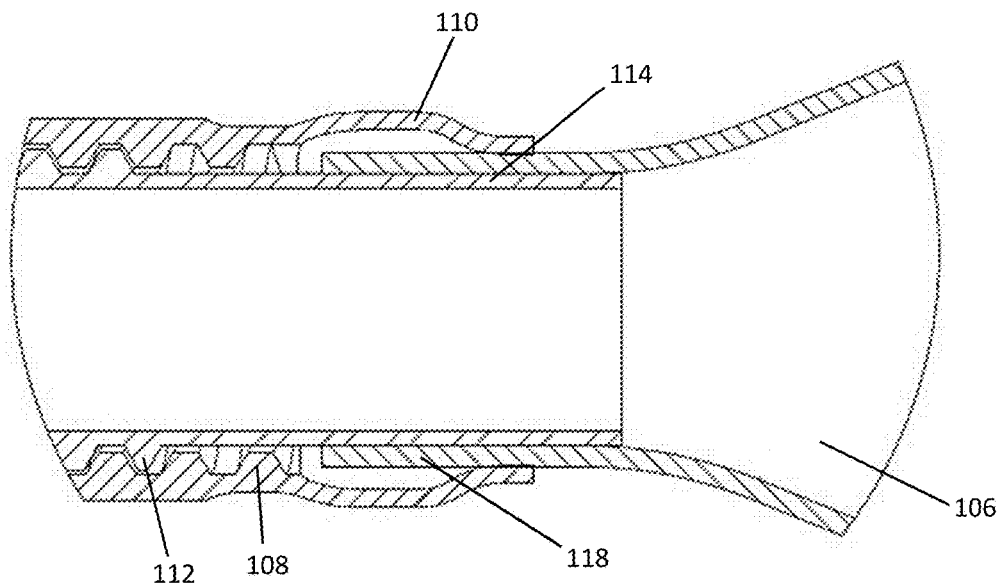
FIG. 6 is a detail view of section A indicated in FIG. 5 in accordance with embodiments of the present invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the spirit and scope of the invention as defined by the appended claims.

DETAILED DESCRIPTION

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention.

It should be appreciated that dimensional relationships among individual elements in the attached drawings are illustrated only for ease of understanding, but not to limit the actual scale.

Referring to FIGS. 1-9, the implant retention system 100 generally includes an elongated hollow mesh tip 102 disposed over an elongated hollow lock tube 104. A knit implant 106 is engaged with the mesh tip 102 and lock tube 104, as described herein, to retain the knit implant 106 to the lock tube 104 during a filling procedure.

Note that the knit implant 106 is depicted in the drawings as a smooth-walled balloon device for simplicity of depiction. It should be understood that the present invention can be utilized or applied to a variety of surgical implants, including knit implants used in spinal surgical procedures, as well as balloons and the like. One example knit implant is disclosed in U.S. Pat. No. 5,549,679, which is hereby incorporated by reference in its entirety.

The mesh tip 102 includes an internal thread section 108 adjacent to a flanged section 110 at the distal end thereof. The lock tube 104 includes a corresponding male threaded section 112 on an exterior thereof that is adjacent to a non-threaded section 114 at the distal end thereof.

A portion of the knit implant 106 defining a filling aperture 118 is slid proximally over the non-threaded section 114 of the lock tube 104. Then the mesh tip 102 is moved distally over the lock tube 104 and is rotated to thread onto the threads of the lock tube 104. In this state, depicted in FIGS. 2-6, a portion of the knit implant 106 is disposed between the distal flanged section 110 of the mesh tip 102 and the distal non-threaded section 114 of the lock tube 104. The flanged section is then mechanically crimped inward against the lock tube 104 to securely retain the implant 106.

Figure 7:
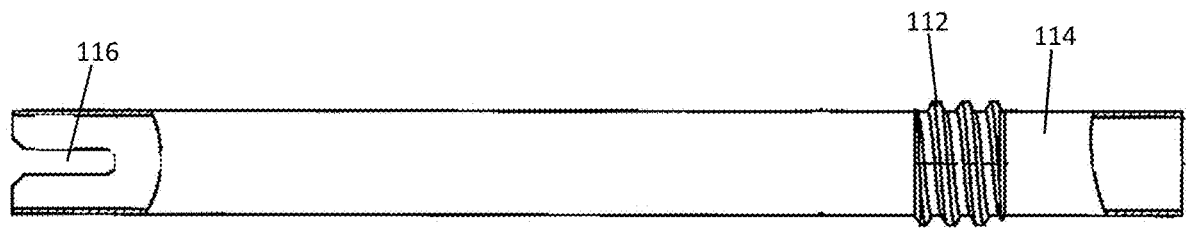
FIG. 7 is a side view of a lock tube of an implant retention system in accordance with embodiments of the present invention.
Figure 8:
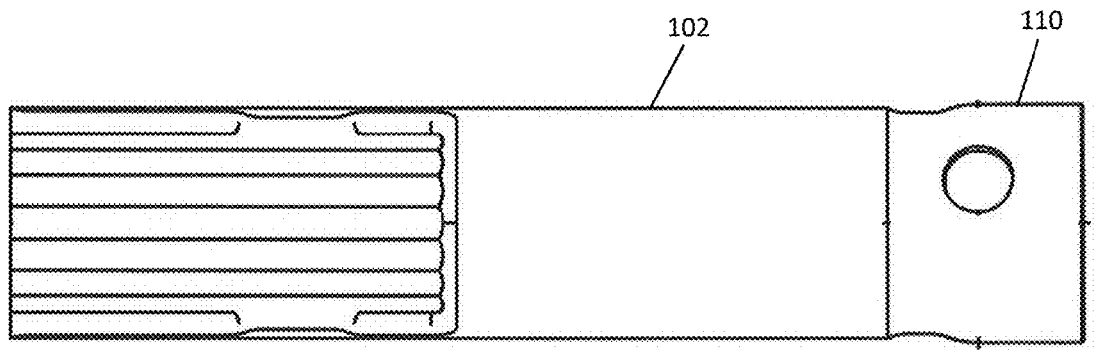
FIG. 8 is a side view of a mesh tip of an implant retention system in accordance with embodiments of the present invention.
Figure 9:
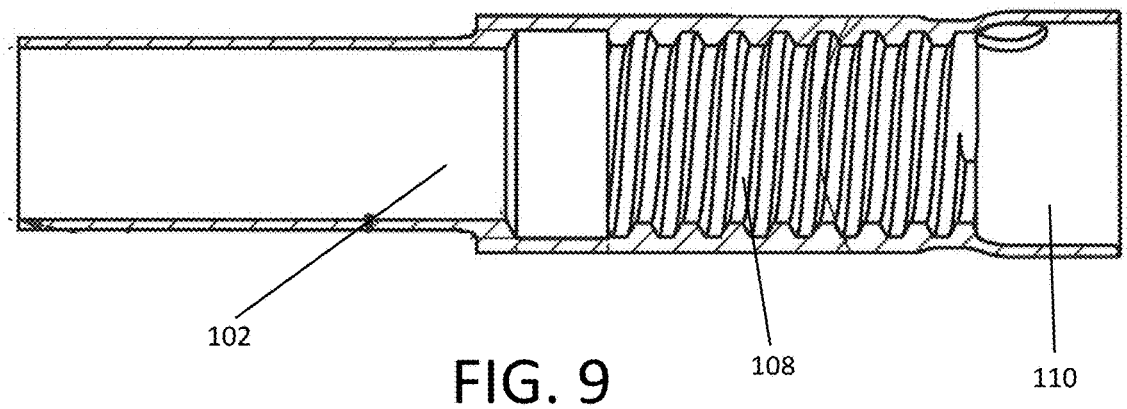
FIG. 9 is a side cross-sectional view of a mesh tip of an implant retention system in accordance with embodiments of the present invention.
Figure 10:
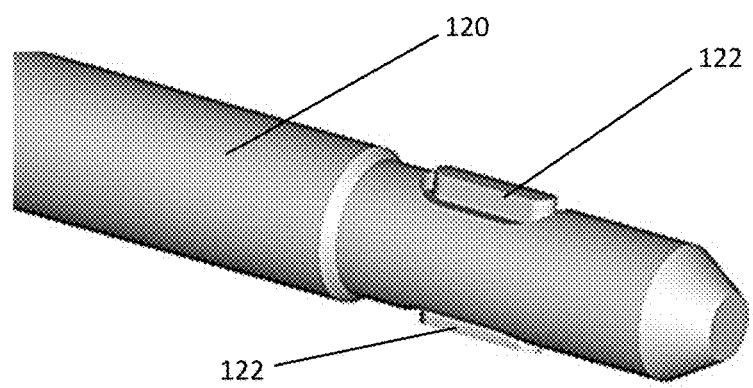
FIG. 10 is a perspective view of a tip portion of a screwdriver for an implant retention system in accordance with embodiments of the present invention.

As shown in FIG. 7, the lock tube 104 also includes female screwdriver slots 116 defined into a proximal end thereof. As shown in FIG. 9, a screwdriver 120 instrument is provided that includes corresponding male projections 122 on a distal end thereof to engage the female screwdriver slots 116 of the lock tube.

To release the implant 106 from its secured position, the screwdriver 120 is disposed through the instrument assembly such that the male projections 122 engage the female screwdriver slots 116. The screwdriver 120 is rotated to rotate the lock tube 104 relative to the mesh tip 102, thereby moving the lock tube 104 relatively proximally due to the threads until the respective threads are fully disengaged. At this state, the implant will no longer be entrapped and instrument components 102, 104 can be withdrawn.

Figure 11:
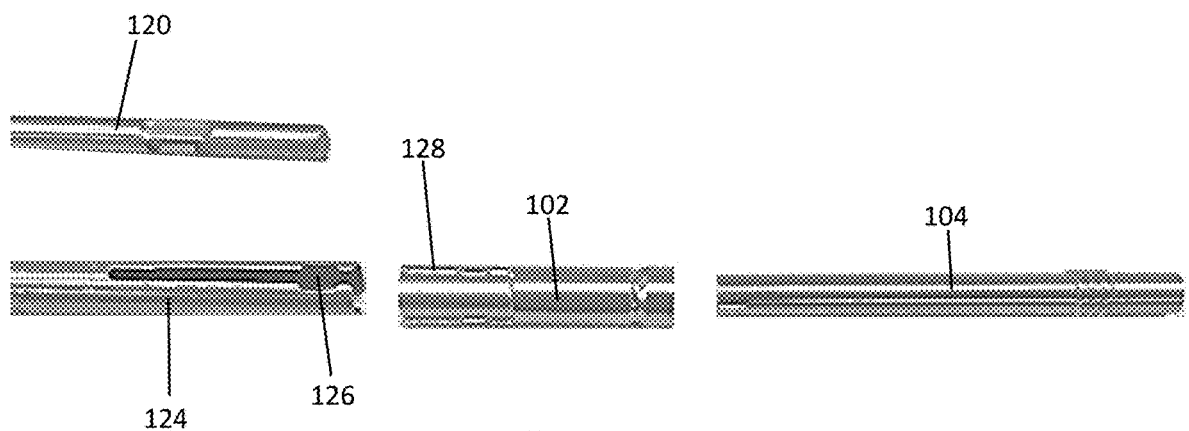
FIG. 11 is a top view of separated components of an implant retention system in accordance with embodiments of the present invention.

Referring to FIG. 11, a positioning retention tube 124 can also be provided to engage with the proximal end of the mesh tip 102 in order to provide the desired amount of distal projection of the lock tube 104 into the implant site (e.g. disc space) in the patient. The distal end of the positioning retention tube 124 defines slots 126 that mate with corresponding ribs 128 defined on a distal section of the exterior surface of the mesh tip 102.

The instrument components described herein can be formed of a variety of rigid materials suitable for surgical procedures, including surgical steels, plastic materials such as polyetheretherketone (PEEK), and combinations thereof.

The instrument components described herein can be combined together in a kit along with one of more spinal implants. A set of instructions for use can also be included in the kit.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:

1. An implant retention system for a knit surgical implant, comprising:
   an elongated hollow mesh tip, including a flanged section at a distal end thereof and an internal threaded section proximal to the flanged section; and
   an elongated hollow lock tube, including a non-threaded section at a distal end thereof and an external threaded section proximal to the non-threaded section,
   wherein the mesh tip is threaded over the lock tube to define a crimp section between the flanged section and the non-threaded section that engages a proximal portion of the knit surgical implant to retain the knit surgical implant in engagement with a distal end of the lock tube until the knit surgical implant is released by unthreading the lock tube from the mesh tip.

2. The system of claim 1, wherein the hollow mesh tip further includes an external rib disposed adjacent to a proximal end thereof.

3. The system of claim 2, further comprising a positioning retention tube, including a slot at a distal end thereof that is sized and shaped to mate with the proximal end of the hollow mesh tip.

4. The system of claim 1, further comprising a positioning retention tube that is configured to mate with a proximal end of the mesh tip.

5. The system of claim 1, wherein the lock tube includes a slot defined in a proximal end thereof.

6. The system of claim 5, further comprising a screw driver, including a male projection sized and shaped to engage the slot of the lock tube.

7. The system of claim 1, further comprising a screw driver configured to engage a proximal end of the lock tube.

8. The system of claim 1, further comprising the knit surgical implant crimped between the flanged section of the mesh tip and the non-threaded section of the lock tube.

9. A method of operating spinal surgical instruments, the method comprising:
   placing a portion of a flexible spinal implant over a distal non-threaded end section of an elongated hollow lock tube;
   threading an elongated hollow mesh tip component over the elongated hollow lock tube component to locate a portion of the flexible spinal implant between a distal flanged section of the mesh tip and the distal non-threaded section of the lock tube;

crimping the flanged section towards the distal non-threaded section to secure the flexible spinal implant relative to the distal non-threaded end section of the lock tube; and releasing the flexible spinal implant from the lock tube by unthreading the mesh tip from the lock tube.

10. The method of claim 9, further comprising:

engaging a screw driver with a proximal end of the lock tube; and rotating the screw driver to unthread the lock tube from the mesh tip until the flexible spinal implant is no longer secured relative to the lock tube.

11. The method of claim 9, further comprising engaging a positioning retention tube with a proximal end of the mesh tip to extend the lock tube into a disc space in a patient.

12. A spinal implant kit, comprising:

a spinal fusion implant;

an elongated hollow mesh tip instrument, including a flanged section at a distal end thereof and an internal threaded section proximal to the flanged section; and an elongated hollow lock tube instrument, including a non-threaded section at a distal end thereof and an external threaded section proximal to the non-threaded section, wherein the mesh tip instrument is configured to be threaded over the lock tube instrument to define a crimp section between a distal end portion of the flanged section and a distal end portion of the non-threaded section so that a portion of the spinal fusion implant can be disposed in the crimp section.

13. The kit of claim 12, wherein the spinal fusion implant is a knit implant.

14. The kit of claim 12, wherein the mesh tip instrument further includes an external rib disposed adjacent to a proximal end thereof.

15. The kit of claim 14, further comprising a positioning retention tube instrument, including a slot at a distal end thereof that is sized and shaped to mate with the proximal end of the mesh tip instrument.

16. The kit of claim 12, further comprising a positioning retention tube instrument that is configured to mate with a proximal end of the mesh tip instrument.

17. The kit of claim 12, wherein the lock tube instrument includes a slot defined in a proximal end thereof.

18. The kit of claim 17, further comprising a screw driver instrument, including a male projection sized and shaped to engage the slot of the lock tube instrument.

19. The kit of claim 12, further comprising a screw driver instrument configured to engage a proximal end of the lock tube instrument.

20. The kit of claim 12, wherein the spinal fusion implant is crimped between the flanged section of the distal end portion of the flanged section of the mesh tip instrument and the non-threaded section of the distal end portion of the non-threaded section of the lock tube instrument.

* * * * *